(12) United States Patent
Zoppetti et al.

(10) Patent No.: US 6,288,044 B1
(45) Date of Patent: Sep. 11, 2001

(54) O-SULFATED BACTERIAL POLYSACCHARIDES

(75) Inventors: Giorgio Zoppetti; Pasqua Oreste; Giovanni Cipolletti, all of Milan (IT)

(73) Assignee: INALCO S.p.A., Milan (IT)

( * ) Notice: Subject to any disclaimer, the term of this patent is extended or adjusted under 35 U.S.C. 154(b) by 0 days.

(21) Appl. No.: 09/355,211

(22) PCT Filed: Feb. 4, 1998

(86) PCT No.: PCT/EP98/00598

§ 371 Date: Jul. 23, 1999

§ 102(e) Date: Jul. 23, 1999

(87) PCT Pub. No.: WO98/34958

PCT Pub. Date: Aug. 13, 1998

(30) Foreign Application Priority Data

Feb. 7, 1997 (IT) .............................. MI97A0252

(51) Int. Cl.$^7$ ................ A61K 31/715; C08B 37/00; C07H 1/00
(52) U.S. Cl. .............. 514/54; 514/56; 536/18.7; 536/21; 536/123.1; 536/124
(58) Field of Search ............ 536/18.7, 21, 123.1, 536/124; 514/54, 56

(56) References Cited

U.S. PATENT DOCUMENTS 5,550,116 * 8/1996 Lormeau et al. .................. 514/56

OTHER PUBLICATIONS

Biotechnology Letters, vol. 18, No. 4 (Apr. 1996), p. 383–386; "Production and Purification of an Extracellularly Produced K4 Polysaccharide from *E. coli*"; M. Manzoni et al.

Eur. J. Biochem., 177 (1988), 117–124; "Structure and Serological Characteristics of the Capsular K4 Antigen of *E. coli* 05:K4:H4, a Fructose–Containing Polysaccharide with a Chondroitin Backbone"; B. Rodriguez M.R. et al.

Carbohydrate Research, 150 (1986) 233–240; "Structure of the Serine–Containing Capsular Polysaccharide K40 Antigen from *E. coli* 08:K40:H9"; Thomas Dengler et al.

Carbohydrate Research, 193 (1989) 165–172; "Reactivity Toward Chemical Sulfation of Hydrozyl Groups of Heparin"; Akira Ogamo, et al.

Carbohydrate Research, 210 (1991) 299–310; "Sulfation of Some Chemically–Modified Heparins—Formation of a 3–Sulfate Analog of Heparin"; Rabindra N. Rej et al.

* cited by examiner

*Primary Examiner*—Kathleen Kahler Fonda
(74) *Attorney, Agent, or Firm*—Hedman & Costigan, P.C.

(57) ABSTRACT

Process for the preparation of O-sulfated K4, K5 and K40 polysaccharides useful for the treatment of tumoral, HIV-1 and coagulation pathologies and in cosmetic preparations, wherein the K4, K5 or K40 polysaccharide in the form of sodium salt is suspended in an aprotic solvent and directly submitted to the reaction of O-sulfation with a pyridine-sulphur trioxide or trimetylamine-sulphur trioxide adduct or with chlorosulfonic acid.

7 Claims, 5 Drawing Sheets

O-SULFATED BACTERIAL POLYSACCHARIDES

This is the U.S. national stage entry under 35 U.S.C. 371 of PCT/EP98/00598, filed Feb. 4, 1998.

PRIOR ART

The bacterial polysaccharides identified as K4, K5 and K40, consisting of repeating sequences of D-glucuronic acid and amino sugars are known. They are obtained according to known techniques by fermentation of different strains of *E. coli* as it is described in several papers (Manzoni M., Bergomi S., F. and Cavazzoni V. Biotechnology Letters 18 (4) 383–386 (1996); B. Rodriguez M. R. et al., Eur. J. Biochem., 177 (1988) 117–124; and Dengler T. et al., Carb. Res., 150 (1986) 233–240).

Moreover, the O-sulfation processes studied for other polysaccharides as by example for heparin after complete desulfation are known.

Said processes provide for a preliminary treatment suitable to remove from the polysaccharide its natural counter-ion (usually sodium) in order to substitute it with tributyl ammonium hydroxide (Ogamo et al. Carb. Res. 193 (1989) 165–172) or with pyridine (Rej et al., Carb. Res. 210 (1991) 299–310) in order to make the polysaccharide itself soluble in solvents as the dimethylformamide or the dimethylsulfoxide.

Said processes require several steps among which an expensive liophilization step too. Moreover they exhibit several drawbacks as for example the weight doubling due to the counter-ion.

SUMMARY

We found that it is possible to obtain the O-sulfated K4, K5 and K40 polysaccharides by a process wherein said polysaccharides in the form of sodium salts are directly sulfated in a suspension in an organic solvent. The process according to the present invention includes the following steps:

a) suspension of the polysaccharide in the form of sodium salts in an aprotic solvent;
b) O-sulfation with a pyridine-sulphur trioxide or trimethylamine-sulphur trioxide adduct or with chlorosulfonic acid;
c) dilution with water;
d) pH adjustment to a basic value;
e) precipitation by addition of ethanol saturated with sodium acetate;
f) dissolution by a NaCl solution;
g) diafiltration;
h) precipitation of the product by alcohols as ethanol or methanol or isopropanol or by acetone;
i) drying.

Optically K4 is preliminary defructosilated.

By the process according to the present invention polysaccharides having a molecular weight ranging from 4,000 to 35,000 and a sulfates/carboxyls ratio ranging from 0.5 to 4.0 are obtained.

The O-sulfated polysaccharides according to the present invention show an interesting anti-angiogenetic and antiviral as well as anticoagulant activity. Moreover they are effective in the cosmetic art in the prevention of hair falling out.

DETAILED DESCRIPTION OF THE INVENTION

Figure 1:
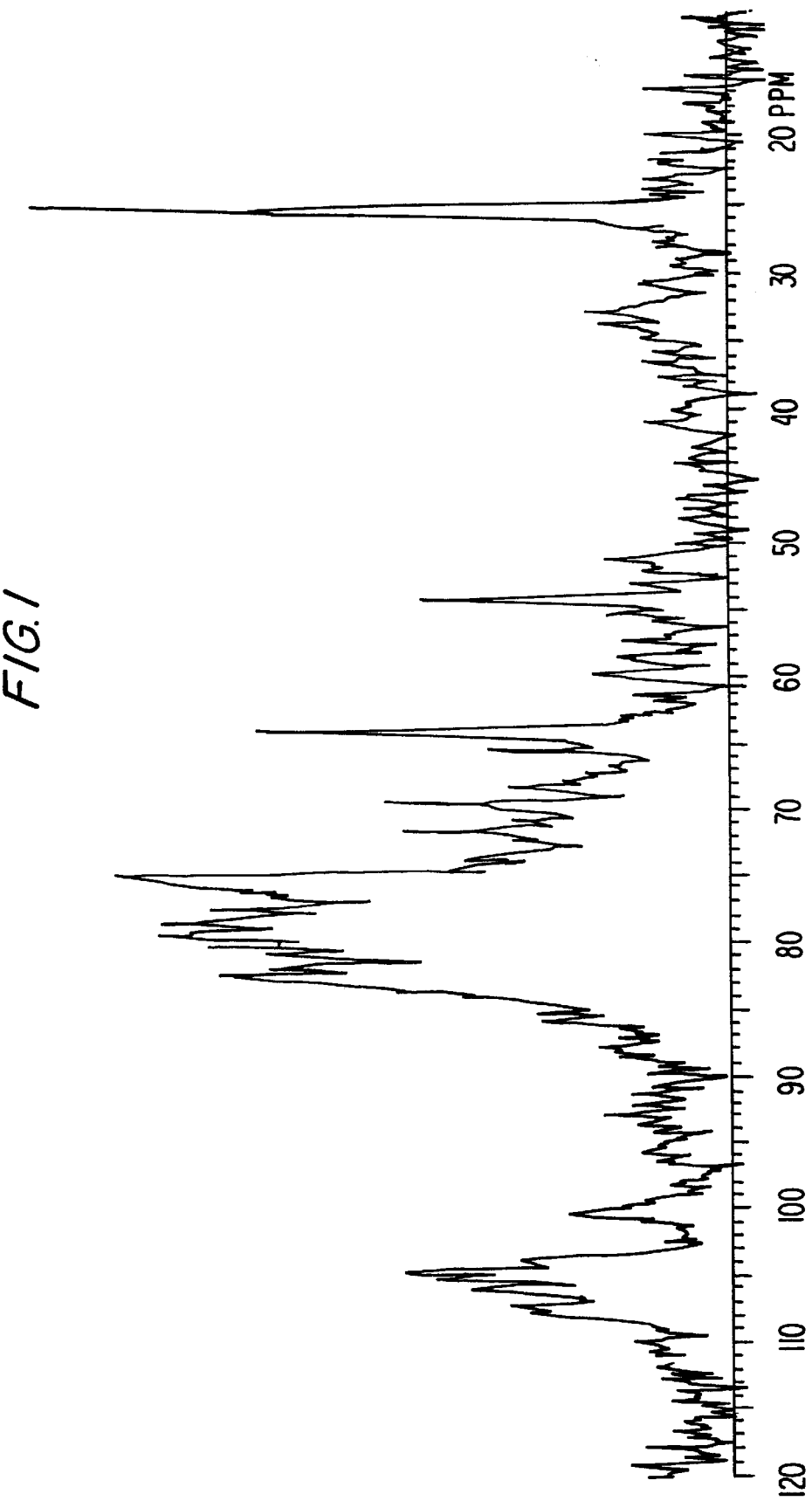
FIG. 1 shows a C13 NMR spectrum of the compound of Example 7.

The characteristics and the advantages of the process for the preparation of the O-sulfated bacterial polysaccharides and of the products obtained acting according to the present invention will be shown mostly during the following detailed description.

In the present invention the starting material is formed by the bacterial polysaccharides obtainable from *E. coli* defined respectively as K4, K5 and K40. The K5 polysaccharide is formed by D-glucuronic acid and by N-acetyl glucosamine linked by a $\alpha 1$–4 bond. The bond between the disaccharides is $\beta 1$–4. The K4 polysaccharide is formed by D-glucuronic acid and by N-acetyl galactosamine linked by a $\beta 1$–3 bond. The bond between the disaccharides is $\beta 1$–4. The K4 polysaccharide contains also a unit of D-fructose bound with a $\beta 2$–3 bond to the D-glucuronic acid. The K40 polysaccharide is formed by trisaccharides consisting of D-glucuronic acid linked to N-acetyl glucosamine by a $\alpha 1$–4 bond linked in turn to another N-acetyl glucosamine by a $\alpha 1$–6 bond. The bond between the trisaccharides is of $\beta 1$–4 kind. The K40 polysaccharide contains also a unit of serine bound to the glucuronic acid carboxyl.

In the process according to the present invention said polysaccharides, in the form of sodium salts, are added at room temperature with an aprotic solvent in order to form a suspension. Said solvent is preferably selected from the group consisting of dimethylformamide, dimethylacetamide and dimethylsulfoxide. Mixtures of these solvents may be used too. The amount of the used solvent is ranging from 10 to 80 parts by weight with respect to the polysaccharide.

For the reaction of O-sulfation, a solution consisting of an amount ranging from 10 to 50 parts by weight with respect to said polysaccharide, of the same solvent used to prepare said suspension, and by an amount ranging from 0.5 to 20 parts by weight with respect to said polysaccharide, of a pyridine-sulphur trioxide of trimethylamine-sulphur trioxide adduct or with chlorosulfonic acid, is added to the obtained suspension.

The reaction is carried out under stirring at a temperature ranging from 0 to 70° C., and preferably between 15 and 35° C., for a time ranging from 2 to 24 hours. When the reaction time is finished, the obtained suspension is diluted by an equal volume of water or of NaCl solutions from 0.1 to 1 N and then the pH is taken to a value ranging from 7.5 to 8.5 by the addition of a 3–6% by weight NaOH aqueous solution.

The product is precipitated by the addition of 1.5–3 volumes of ethanol saturated with sodium acetate and maintaining the mixture at a temperature equal to 3–5° C. for 12–15 hours. The obtained precipitate is dissolved into 100 parts by weight of a 2N sodium chloride solution and the solution is diafiltered by 10 volumes of distilled water using a cut-off 3000 dialysis cartridge with TFF millipore system. The product is precipitated by the addition of 2–4 volumes of ethanol and then it is dried at a temperature equal to 60°

C., at reduced pressure. When one wants to obtain a product having characteristics of anti-HIV activity the starting K4 polysaccharide is preliminarly defructosilated for example by the method described by B. Rodriguez M. R. et al. (Eur. J. Biochem., 177 (1988), 117–124).

The O-sulfated polysaccharides according to the present invention are analyzed by conductometric titration, $^{13}$C-NMR and $^1$H-NMR spectroscopy and HPLC. In particular, their molecular weight is determined by HPLC.

The O-sulfated polysaccharides according to the present invention are characterized by a molecular weight ranging from 4,000 to 35,000 and by a sulfates/carboxyls ratio ranging from 0.5 to 4.0.

The compounds according to the present invention show a good anti-angiogenetic activity whereby they may be used in the control of the tumoral growth and of the metastasis formation.

Moreover they show a good anticoagulant activity. Finally the mostly sulfated compounds (sulfates/disaccharide >2.5) and in the case of the defructosilated K4 they show an interesting anti-HIV-1 activity.

Thanks to these characteristics they may be successfully used in the human therapy.

The compounds according to the present invention, besides for therapeutic purpose for the above reported indications, they may be used also in the cosmetic field with the function of coadiuvants in the prevention of the hair falling out. For the expected therapeutic or cosmetic uses the derivatives obtainable according to the process of the invention are formulated according to the conventional techniques in suitable administration forms such as for example sterile solutions, topic dosage forms and, in general, in all those forms until today proposed for the derivatives of polysaccharidic kind or of glycosaminoglycans. In particular for the therapeutic use with anti-angiogenetic, anticoagulant and anti-HIV-1 purpose the efficacious doses are ranging from 0.1 to 10 mg/kg/day. The following Examples are reported for illustrative aim of the invention.

EXAMPLE 1

O-sulfation of the K4 polysaccharide 1 g of K4 sodium salt obtained by fermentation (as described by Manzoni, M., Bergomi, S Molinari, F., & Cavazzoni, V (1996) Production and Purification of an Extracellularly Produced K4 Polysaccharide from Escherichia Coli. Biotechnology Letters, 18, 383–386) is suspended in 60 ml of anhydrous dimethylformamide at room temperature and 40 ml of anhydrous dimethylformamide containing 15.3 g of pyridine-sulphur trioxide adduct are then added. The obtained suspension is maintained at room temperature, under stirring, for 18 hours and then diluted with an equal volume of water. The pH is taken to 9 with 4% NaOH and the product is precipitated by 2 volumes of ethanol saturated with sodium acetate maintaining the solution at 4° C. for 12 hours. The obtained precipitate is dissolved in 100 ml of 2N sodium chloride and diafiltered by 10 volumes of distilled water using a cut-off 3000 dialysis cartridge with TFF millipore system.

Finally the product is precipitated by 3 volumes of ethanol and dried at a temperature equal to 60° C. at reduced pressure.

The obtained product shows a sulfates/carboxyls ratio equal to 3 and an average molecular weight equal to 28,000 d.

EXAMPLE 2

O-Sulfation of the Defructosilated K4 Polysaccharide 1 g of K4 sodium salt is defructosilated as described by B. Rodriguez M. R. et al. and then treated as described in the Example 1.

The obtained product shows a sulfates/carboxyls ratio equal to 1.2 and an average molecular weight equal to 35,000 d.

EXAMPLE 3

O-Sulfation of the K5 Polysaccharide 1 g of K5 sodium salt obtained by fermentation as described by Manzoni M. et al. is treated as in the Example 1.

The obtained product shows a sulfates/carboxyls ratio equal to 3.5 and an average molecular weight equal to 11,000 d.

EXAMPLE 4

O-Sulfation of the K40 Polysaccharide 1 g of K40 sodium salt obtained by fermentation as described by Dengler T. et al. is treated as in the Example 1.

The obtained product shows a sulfates/carboxyls ratio equal to 3 and an average molecular weight equal to 32,000 d.

EXAMPLE 5

O-Sulfation of K5 with Chlorosulfonic Acid 1 g of K5 sodium salt obtained by fermentation as described by Manzoni M. et al. is dried at 60° C. at reduced pressure for 24 hours and dissolved by slow stirring in 30 ml of a previously prepared mixture of sulfuric acid-chlorosulfonic acid in a 2:1 ratio and it is maintained at −4° C. The mixture is left for 60 minutes under stirring at −4° C. and for other 60 minutes at room temperature. The product is recovered neutralizing with 5N NaOH controlling the temperature by a refrigerated bath. Then the solution is desalted using a cut-off 3000 dialysis cartridge with TFF millipore system. Finally the product is precipitated with 3 volumes of ethanol and dried.

The obtained product shows a sulfates/carboxyls ratio equal to 3.3 and an average molecular weight equal to 4,000 d.

EXAMPLE 6

O-sulfation of the K4 polysaccharide 1 g of K4 sodium salt obtained by fermentation as described by B. Rodriguez M. R. et al. is dissolved in 60 ml of anhydrous dimethylformamide at room temperature and 40 ml of anhydrous dimethylformamide containing 2.5 g of pyridine-sulphur trioxide adduct are added. The obtained suspension is maintained at room temperature for 8 hours and then diluted with an equal volume of water. The pH is finally taken to 9 by 4% NaOH and the product is precipitated by 2 volumes of ethanol saturated with sodium acetate maintaining the solution at 4° C. overnight. The obtained precipitate is dissolved in 100 ml of 2N sodium chloride and diafiltered by 10 volumes of distilled water using a cut-off 3000 dialysis cartridge with TFF millipore system. Finally the product is precipitated by 3 volumes of ethanol and dried. The obtained product shows a sulfates/carboxyls ratio equal to 1.7 and an average molecular weight equal to 27,000 d.

EXAMPLE 7

O-Sulfation of the Defructosilated K4 Polysaccharide 1 g of K4 sodium salt is defructosilated as described in the Example 2 and treated as described in the Example 6 but with a reaction time equal to 18 hours. Then the purification is carried out as in the Example 1.

The obtained product shows a sulfates/carboxyls ratio equal to 1.88 and an average molecular weight equal to 24,000 d and the carbon 13 NMR outline reported in FIG. 1.

Figure 2:
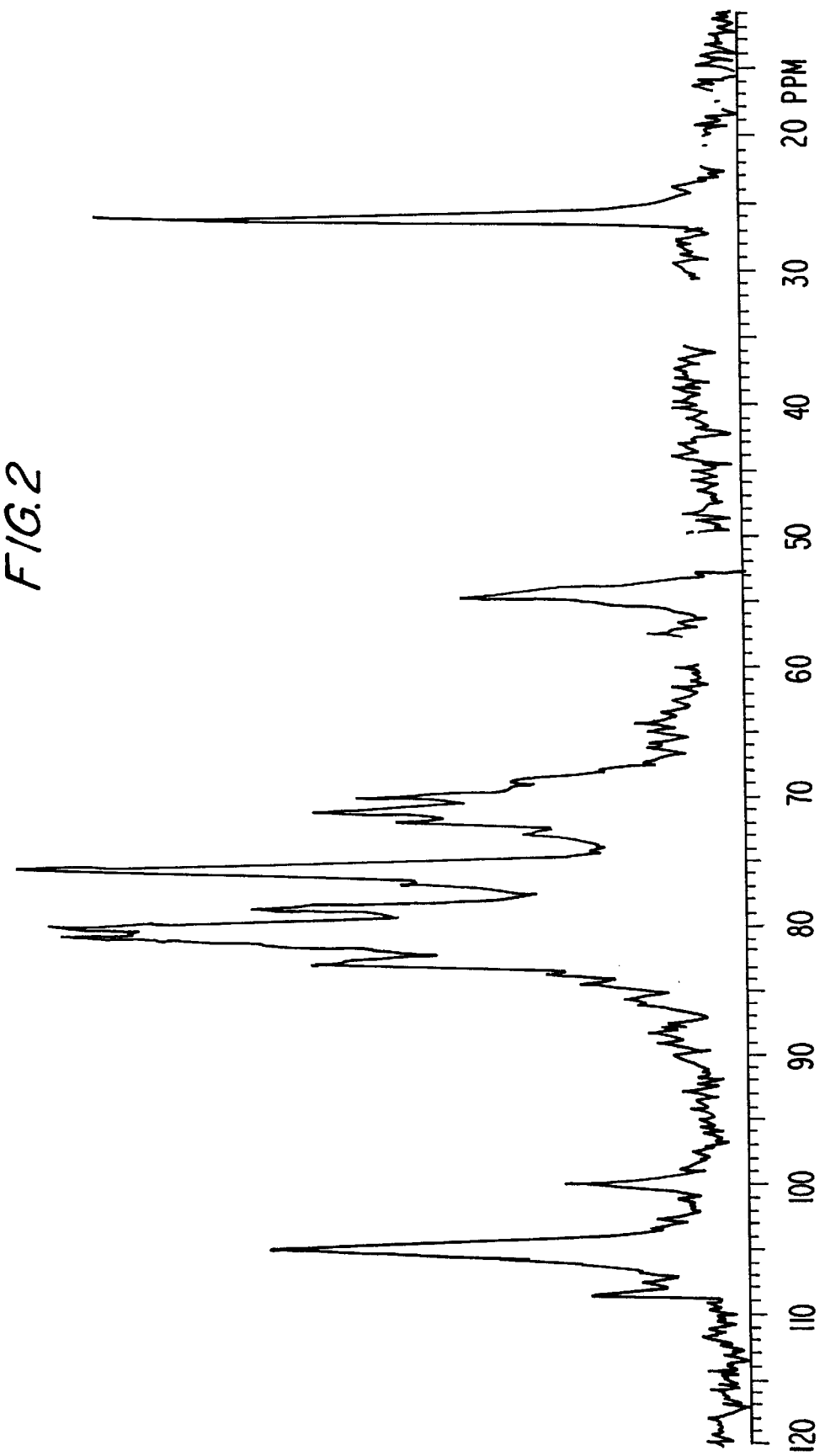
FIG. 2 shows a C13 NMR spectrum of the compound of Example 8.

EXAMPLE 8
O-Sulfation of the Defructosilated K4 Polysaccharide 1 g of K4 sodium salt is defructosilated as described in the Example 2 and treated as described in the Example 6 but with a reaction time equal to 18 hours and adding twice the amount equal to 2.5 of pyridine-sulphur trioxide. Then the purification is carried out as in the Example 1. The obtained product shows a sulfates/carboxyls ratio equal to 3.01 and an average molecular weight equal to 20,000 d and the carbon 13 NMR outline reported in FIG. 2.

EXAMPLE 9
O-Sulfation of the K5 Polysaccharide 1 g of K5 sodium salt obtained by fermentation as described by Manzoni et al. is treated as in the Example 6 but with a reaction time equal to 18 hours and lowering pyridine-sulphur trioxide to 1.75 g. Then the purification is carried out as in the Example 1.

Figure 3:
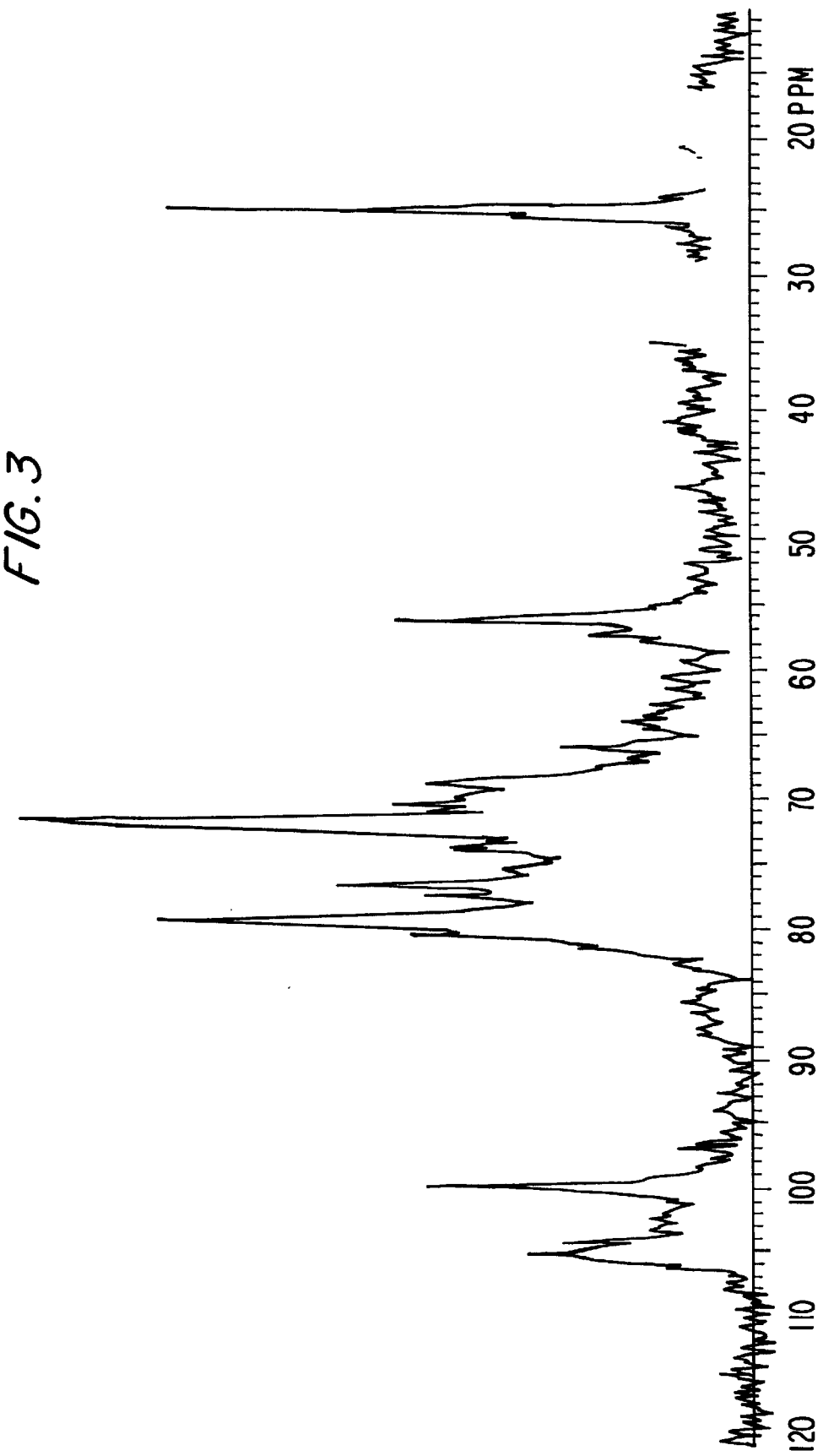
FIG. 3 shows a C13 NMR spectrum of the compound of Example 9.

The obtained product shows a sulfates/carboxyls ratio equal to 2.5 and an average molecular weight equal to 12,000 d and the carbon 13 NMR outline reported in FIG. 3.

Figure 4:
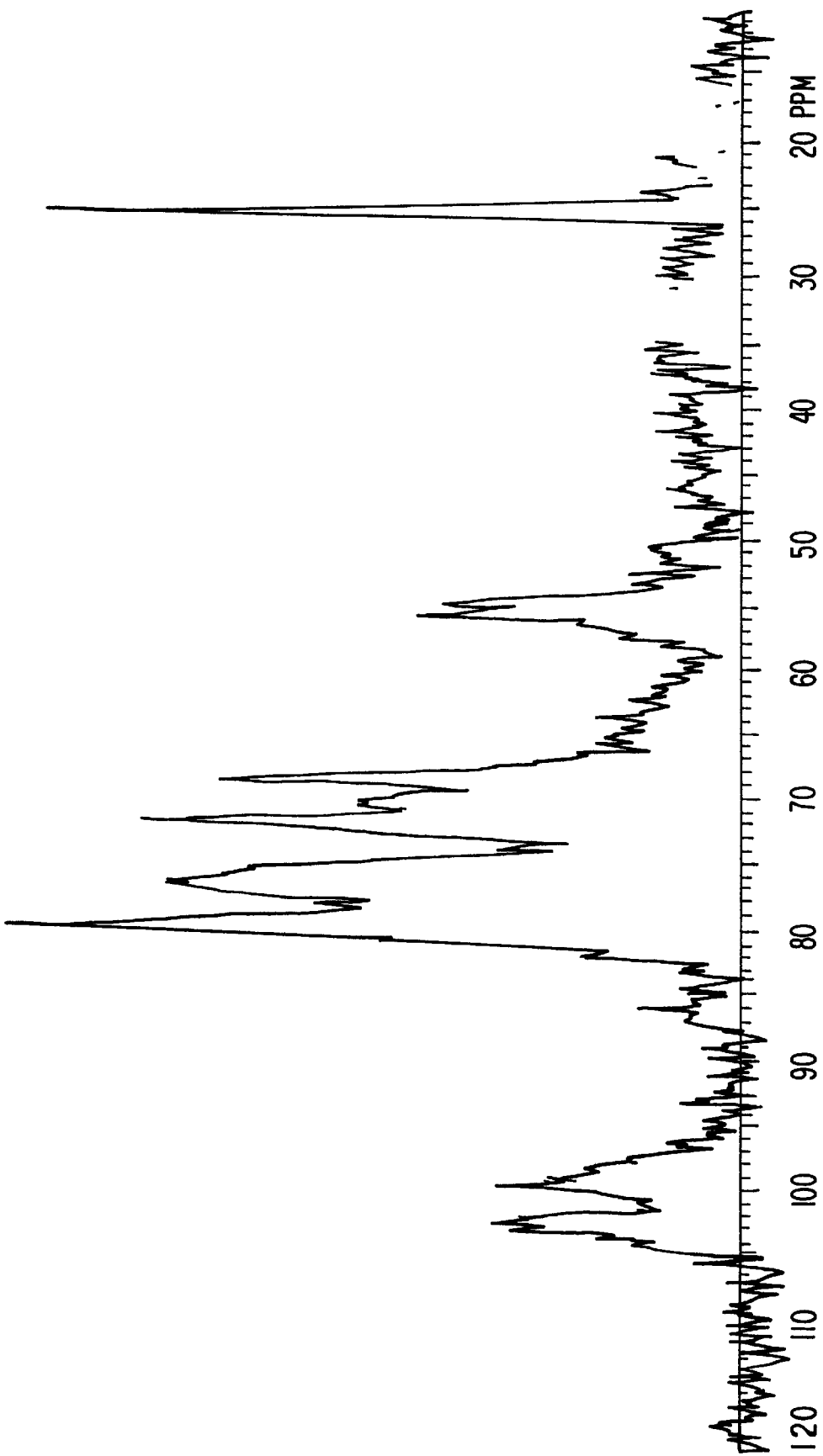
FIG. 4 shows a C13 NMR spectrum of the compound of Example 10.

EXAMPLE 10
O-Sulfation of the K5 Polysaccharide 1 g of K5 sodium salt obtained by fermentation as described by Manzoni et al. is treated as in the Example 6 but with a reaction time equal to 18 hours. Then the purification is carried out as in the Example 1. The obtained product shows a sulfates/carboxyls ratio equal to 3.43 and an average molecular weight equal to 11,000 d and the carbon 13 NMR outline reported in FIG. 4.

Figure 5:
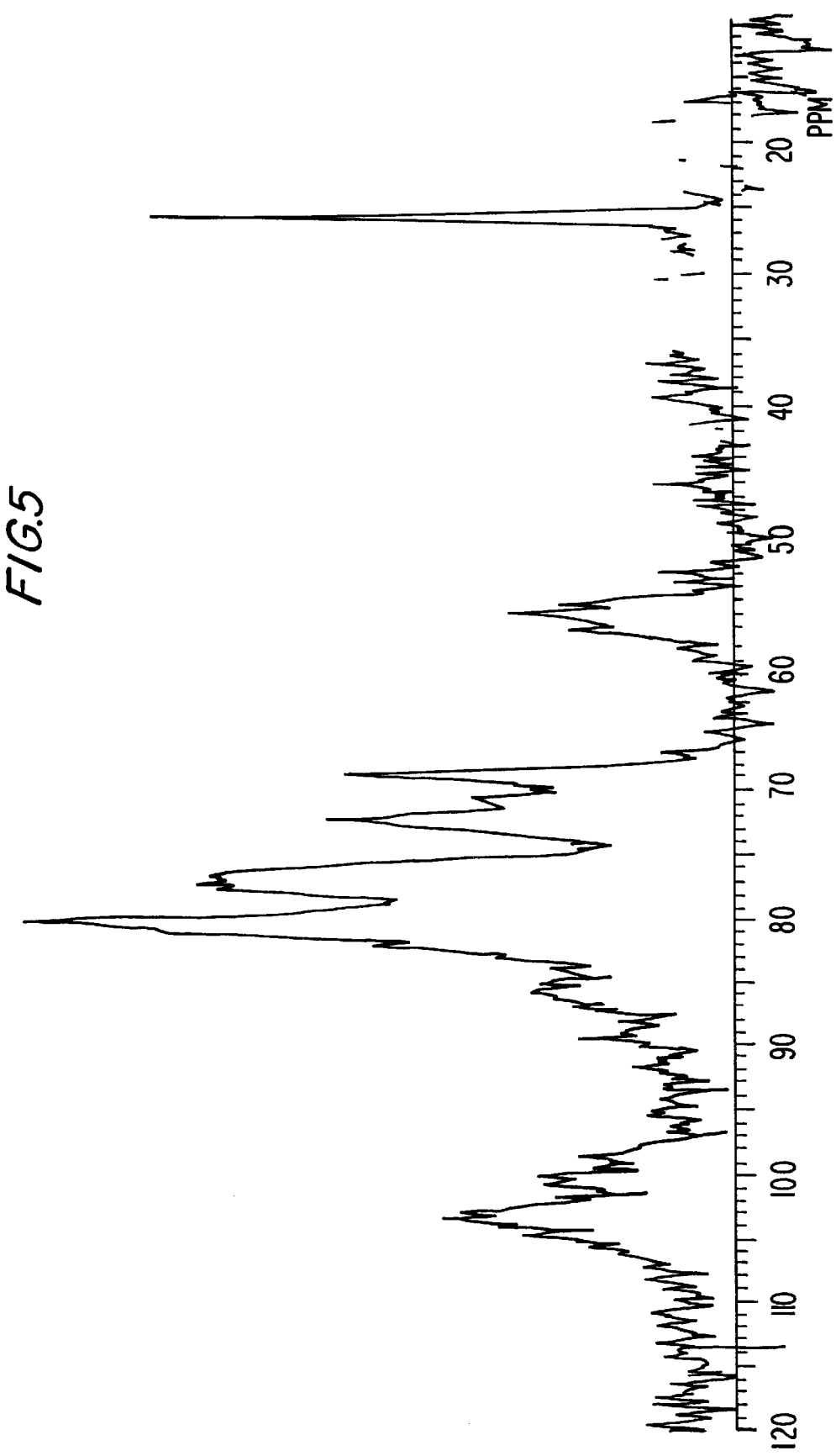
FIG. 5 shows a C13 NMR spectrum of the compound of Example 11.

EXAMPLE 11
O-Sulfation of the K5 Polysaccharide 1 g of K5 sodium salt obtained by fermentation as described by Manzoni et al. is treated as in the Example 10 using instead a halved volume of DMF. Then the purification is carried out as in the Example 1. The obtained product shows a sulfates/carboxyls ratio equal to 4.0 and an average molecular weight equal to 11,000 d and the carbon 13 NMR outline reported in FIG. 5.

EXAMPLE 12
Activity of Hair Growth Stimulation of the O-Sulfated K5 Polysaccharide The sample obtained as described in the Example 11 has been tested for the activity of the anagen phase induction of the hair growth on an animal model (Burgundy red rabbit). The anagen phase of the hair growth in this animal model is directly correlated to the stimulation of the human hair growth. The back hair has been shaved to the animals for an area about equal to 140 cm$^2$. On each animal 5 couples of injections (4 with 0.1 ml of the material under examination at the concentrations of 0.05%, 0.1%, 0.2% and 0.5% and one with sterile water as negative control) have been applied. The injections have been daily repeated for two weeks (5 days on 7). The animals have been daily observed before each administration and for other 25 days after the last inoculation in order to reveal the appearance of dark colour at the cutaneous level and the following growth of dark hair around the injection sites.

The results are reported in the following Table.

| Concentrations | Site 1 | Site 2 | Site 1 | Site 2 | Site 1 | Site 2 |
| --- | --- | --- | --- | --- | --- | --- |
| 0.05 | +++ | ++ | ++ | + | + | + |
| 0.1% | ++ | +++ | +++ | ++ | + | +++ |
| 0.2% | +++ | +++ | +++ | +++ | +++ | +++ |
| 0.5% | ++ | ++ | ++ | ++ | ++ | ++ |
| Distilled water | − | − | − | − | − | − |

EXAMPLE 13
Toxicity and irritation Tests of the O-Sulfated K5 Polysaccharide According to the CEE 92/69 Requirements The sample obtained as described in the Example 11 has been tested in order to determine the toxicity and the irritating power according to the CEE 92/6 standards.

In the following Table are reported the obtained results:

| Study Description | Result | Notes |
| --- | --- | --- |
| Acute Oral Toxicity | $DL_{50} > 2{,}000$ mg/kg | |
| Allergic Irritation (Kligmann Magnusson Test) | Negative | |
| Cutaneous Tolerability (CEE 92/69-B4/OECD 404) | Negative | |
| Ocular Tolerability (CEE 92/69-B5/OECD 405) | Negative | 60 min after the administration the conjunctiva appears on the average congested with a light chemosis. The congestion regresses after 7 days and the chemosis after 24 hours. |
| Mutagenesis (AMES Test) | Negative | |

What is claimed is:

1. Process for preparation of O-sulfated K4, defructosylated K4, K5 and K40 polysaccharides comprising the following steps:
   a) suspension of K4, defructosylated K4, K5 or K40 polysaccharide in the form of a sodium salt in an aprotic solvent;
   b) O-sulfation with a pyridine-sulphur trioxide or trimethylamine-sulphur trioxide adduct or with chlorosulfonic acid;
   c) dilution with water or with 0.2–1 N NaCl;
   d) pH adjustment to a basic value;
   e) precipitation by addition of ethanol saturated with sodium acetate or methanol. isopropanol or acetone;
   f) dissolution by a NaCl solution;
   g) diafiltration;
   h) precipitation of the product by ethanol;
   i) drying.

2. Process as claimed in claim 1, wherein said aprotic solvent used in the step a) is selected from the group consisting of dimethylformamide, dimethylacetamnide and dimethylsulfoxide.

3. Process as in claim 1, wherein said O-sulfation is carried out using an amount of pyridine-sulphur trioxide or trimethylamine-sulphur trioxide adduct or chlorosulfonic acid ranging from 0.5 to 20 parts by weight with respect to said polysaccharide, dissolved in an amount ranging from 10 to 50 parts by weight with respect to said polysaccharide of the same solvent used in the step a).

4. Process as in claim 1, wherein said O-sulfation is carried out at a temperature ranging from 0–70° C. for a time ranging from 2 to 24 hours.

5. Process as in claim 1, wherein said pH adjustment of the step d) [pH] is carried out with an aqueous solution of 2–6% by weight NaOH to reach a pH ranging from 7.5 to 8.5.

6. Process as in claim 1, wherein said precipitation of the step e) is carried out with 1.5–3 volumes of ethanol or methanol or isopropanol or acetone saturated with sodium acetate and maintaining the obtained mixture at a temperature equal to 3–5° C. for 12–15 hours.

7. A therapeutic method for the treatment of tumoral and HIV-1 pathologies wherein doses ranging from 0.1 to 10 mg/kg/day of the O-sulfated K4, defructosylated K4, K5 or K40 polysaccharides having a molecular weight ranging from 4,000 to 35,000 and a sulfates/carboxyls ration ranging from 0.5 to 4 are administered to a patient.

* * * * *